United States Patent [19]

Dryden

[11] 4,256,099
[45] Mar. 17, 1981

[54] TWO-TUBE RESUSCITATION SYSTEM

[76] Inventor: Gale E. Dryden, 5835 N. Tacoma, Indianapolis, Ind. 46220

[21] Appl. No.: 22,639

[22] Filed: Mar. 21, 1979

[51] Int. Cl.³ ............................................. A61M 16/00
[52] U.S. Cl. ........................... 128/200.26; 128/207.15
[58] Field of Search ................. 128/145.5, 147, 145.8, 128/351, 349 B, DIG. 9, DIG. 26, 208, 200.26, 207.14, 207.15

[56] References Cited

U.S. PATENT DOCUMENTS

| | | | |
|---|---|---|---|
| 1,270,565 | 6/1918 | Teter | 128/208 |
| 2,599,521 | 6/1952 | Berman | 128/208 |
| 2,908,269 | 10/1959 | Cheng | 128/351 X |
| 3,683,908 | 8/1972 | Michael | 128/145.7 |
| 3,730,179 | 5/1973 | Williams | 128/145.5 |
| 3,841,319 | 10/1974 | Michael | 128/28 |
| 3,874,377 | 4/1975 | Davidson | 128/145.5 |
| 3,905,361 | 9/1975 | Hewson et al. | 128/145.5 |
| 3,926,458 | 12/1975 | Dryden | 285/177 |
| 3,960,148 | 6/1976 | Dryden | 128/188 |
| 4,090,518 | 5/1978 | Elam | 128/351 X |
| 4,112,936 | 9/1978 | Blachly | 128/208 X |

FOREIGN PATENT DOCUMENTS 1288033 9/1972 United Kingdom.

*Primary Examiner*—Henry J. Recla
*Attorney, Agent, or Firm*—Woodard, Weikart, Emhardt & Naughton

[57] ABSTRACT

Two tubes of flexible, resilient transparent material are introduced side-by-side into the oral cavity. The distal ends of the tubes are longitudinally spaced, so that the more remote end will enter either the esophagus or larynx before the more proximate distal end enters either passageway. A cuff adjacent the more remote distal end is inflated to seal the tube in the passageway. A collar is placed at the mouth and seals the tube at the mouth and is retained in place. A nose clip seals the nasal cavity. Air is introduced to the uncuffed tube. If it is thereby supplied to the trachea, ventilation is continued through that tube. If air is not thereby supplied to the trachea, air is supplied to the cuffed tube, which has entered the trachea, and ventilation is thereupon provided to that tube. Aspiration or administration of material can be provided through whichever tube is not supplying air to the trachea.

8 Claims, 8 Drawing Figures

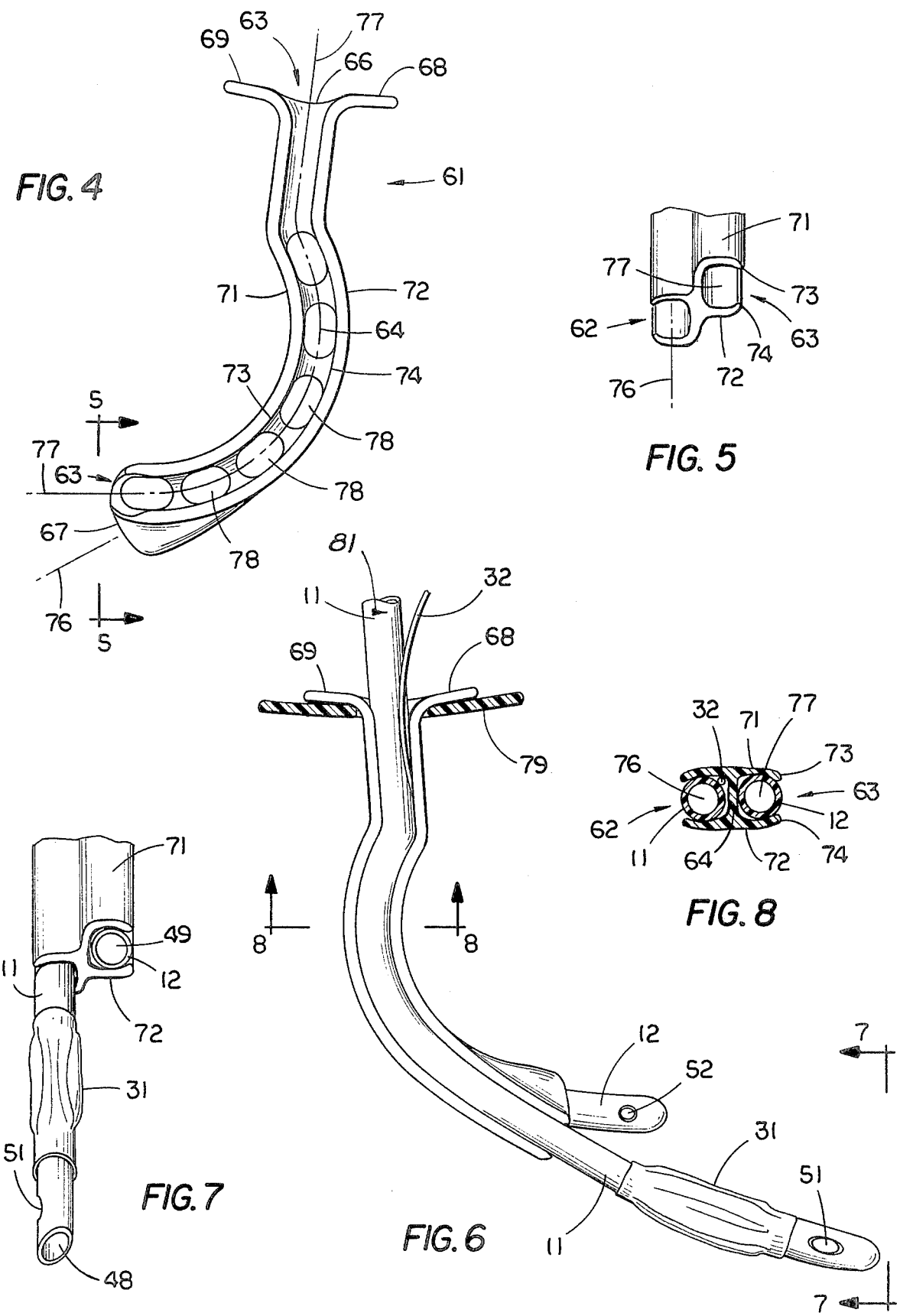

TWO-TUBE RESUSCITATION SYSTEM

BACKGROUND OF THE INVENTION

1. Field of the Invention

This invention relates generally to emergency resuscitation of unconscious people, and more particularly to apparatus and a method of use for such purposes.

2. Description of the Prior Art

There are many emergency situations in which it is necessary to provide artificial ventilation or cardio-pulmonary resuscitation for an unconscious person. It is preferred that an artificial airway be established as promptly as possible in order to avoid the possibility of choking and the necessity for mouth-to-mouth respiration. Some devices for this purpose are described in U.S. Pat. No. 3,683,908 and U.S. Pat. No. 3,841,319 and U.S. Pat. No. 3,905,361, and British Pat. No. 1,288,033. These devices are intended for entry into the esophagus, with the inflation of a cuff in the esophagus to preclude passage of air into the stomach and discharge of contents of the stomach, and thus enable the supplying of air to the trachea. Of course they require the sealing of nasal and oral passageways, so as to avoid loss of air from either of these locations. This is normally accomplished by a mask surrounding the esophageal tube.

These devices can cause particular problems in the event the esophageal tube enters the trachea, instead of the esophagus. They can either interfere with respiration or totally preclude it, and the intubation error must be noted promptly to avoid disastrous results. Of course, this depends upon the skill of the user of the device and, such skills are not always readily available in emergency situations, even where the apparatus is available. The present invention is addressed to overcoming this problem of the prior art devices.

SUMMARY OF THE INVENTION

Described briefly, in a typical embodiment of the present invention, two lumens are provided for simultaneous insertion through the mouth of the subject to be treated, with one having a distal end opening which can be spaced lengthwise from the distal end opening of the other. Means are provided for radially outwardly occluding the passageway into which the more remote portion of the lumen is received so that, in the event it is received in the esophagus, that can be occluded, and in the event it is received in the trachea, the trachea can be occluded radially outwardly of the lumen. In this way, regardless of whether the more remote distal portion enters the esophagus or trachea, there will be no occlusion of the airway to the lungs, and ventilation can be applied without removing the apparatus and reinserting it in an effort to properly locate the lumens.

BRIEF DESCRIPTION OF THE DRAWINGS

FIG. 4 is a side elevational view on an enlarged scale of the preferred form of guide member as employed in the embodiment of FIG. 3.

FIG. 5 is a fragmentary view taken at line 5—5 in FIG. 4 and viewed in the direction of the arrows.

FIG. 6 is an elevational view of the apparatus of FIG. 3 as seen from the opposite side and including the two tubes, with the upper end thereof omitted to conserve space in the drawing.

FIG. 7 is a view taken at line 7—7 in FIG. 6 and viewed in the direction of the arrows.

FIG. 8 is a sectional view taken at line 8—8 in FIG. 6 and viewed in the direction of the arrows.

DESCRIPTION OF THE PREFERRED EMBODIMENT

Figure 1:
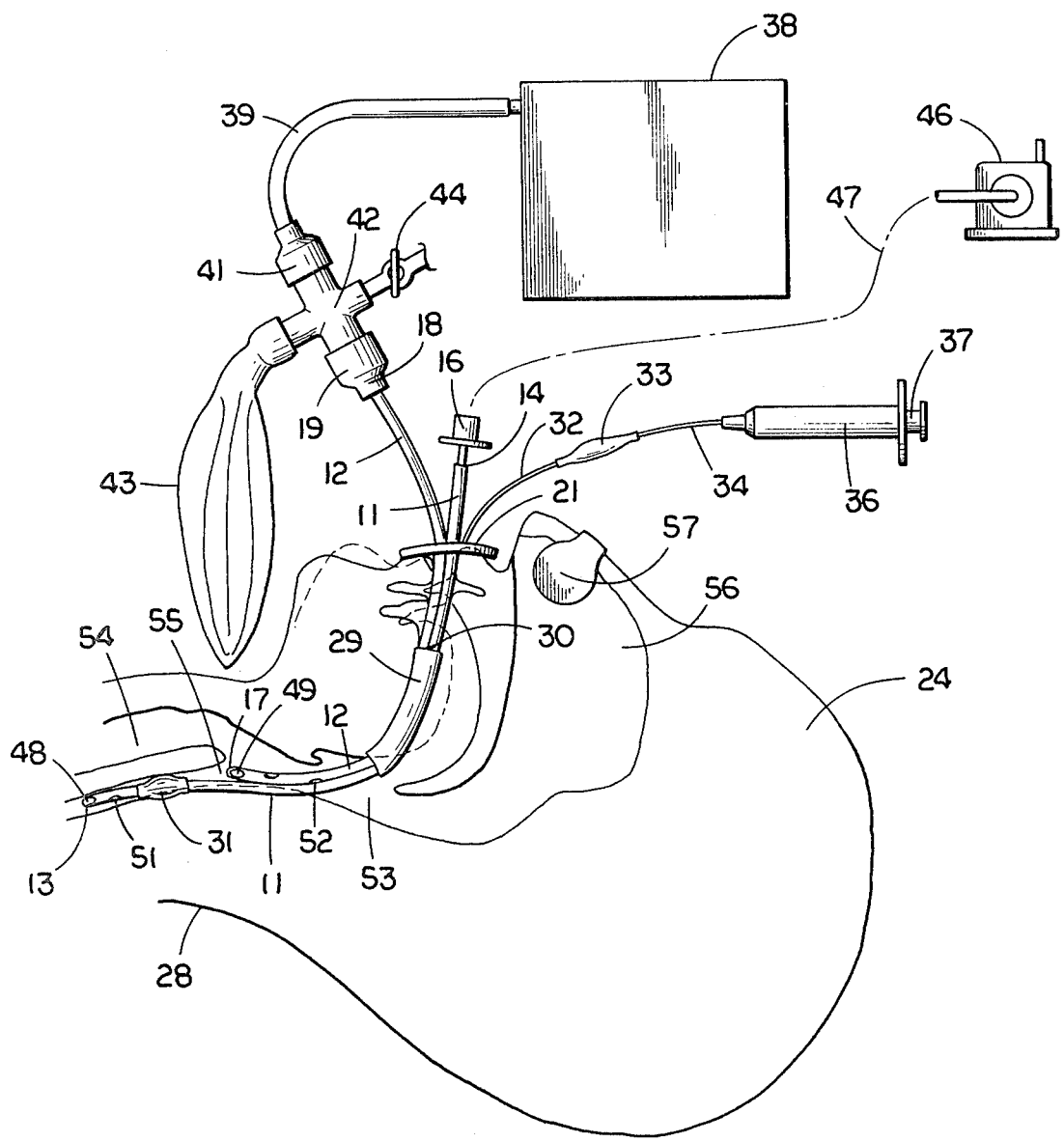
FIG. 1 is a view of the apparatus of one embodiment of the present invention in use.

Referring now to the drawings in detail, and particularly FIG. 1, the apparatus in one form of the present invention includes two tubes 11 and 12, each of which is flexible and resilient, preferably with a slight curve simulating the general curvature of the oral cavity and passageways to the esophagus and trachea, to facilitate insertion through the oral cavity and into the desired passageways. The tubes are preferably transparent, and polyvinylchloride (PVC) is one suitable material.

Tube 11 has a distal end 13 and proximal end 14 with an inside endotracheal tube adaptor 16 at the proximal end. Tube 12 also has a distal end 17 and proximal end 18, with the latter being received by another endotracheal tube or (as illustrated) in an outside endotracheal tube connector 19 of a type such as shown and described in my U.S. Pat. No. 3,926,458 issued Dec. 16, 1975.

A stop collar 21 is provided with a pair of apertures 22 and 23 (FIG. 2), each of which snugly receives one of the two tubes. As the tubes are made of a flexible, resilient material, so is the stop collar made of a flexible resilient material so that, although the collar is snug on the tubes, it can be slid axially of the tubes to accommodate the subject being treated, whose head is shown at 24. The collar has an integral strap 26 which is receivable through a slot 27 which is sufficiently small to snugly receive the strap and retain it securely at any location on the strap. In this way, the strap is easily adjustable around the back of the head of the subject and usually bears at the back of the neck at 28.

A sleeve 29 is affixed to tube 11 and extends snugly around tube 12, although not so tightly as to prevent tube 12 from being slidable longitudinally of tube 11. Sleeve 29 may likewise be made of a resilient, flexible material.

Figure 2:
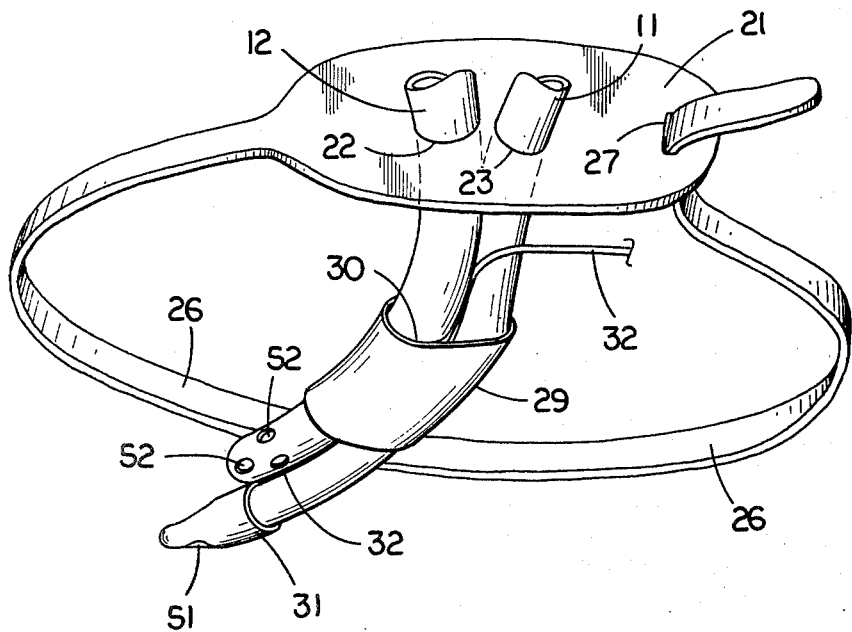
FIG. 2 is a pictorial view of the apparatus before use and on a larger scale and viewing it somewhat axially of the tubes.

An external cuff 31 is provided on tube 11 and communicates through the small tube 32 with an indicator bag 33 and which, in turn, communicates through tube 34 with the syringe 36 having plunger 37 therein and which is operable to inflate or deflate the cuff. FIG. 1 shows the cuff inflated, whereas FIG. 2 shows it substantially deflated.

A ventilating machine 38 is connected through tube 39 and fitting 41 and Tee fitting 42 and connector 19 to the tube 12. A breathing bag 43 is connected to fitting 42 and a valve 44 is also connected to this fitting. An aspirating machine 46 may be connected as indicated by the dotted line 47 to the tube 11.

FIG. 1 illustrates that the distal end 17 of tube 12 is spaced longitudinally of tube 11 from the distal end 13 of tube 11. This distance may be approximately 10 cm. The overall lengths of the tubes 11 and 12 may be approximately 30 cm. and 15 cm., respectively. Tube diameter may typically be 5–10 mm inside diameter (I.D.). In addition to the end apertures 48 and 49 in tubes 11 and 12, a side wall aperture 61 is provided in tube 11, and a plurality of longitudinally and circularly spaced side wall apertures 52 is provided in tube 12. The purpose of these will become apparent upon consideration of the procedure according to the present invention.

The subject being treated will likely be unconscious. Consequently, the larynx will be open. As a result, during normal intubation procedures where a device of the type shown in U.S. Pat. No. 3,683,908 may be employed, there is the possibility that the tip of the esophageal tube, being curved, will pass through the pharynx 53 and enter the larynx 54. Then, upon inflating the cuff of that device, the trachea will be sealed, contrary to the intent of the rescue person. The observant technician will likely note the problem of administering air through the apparatus, remove the apparatus, and reinsert it, in an effort to have the tip enter the esophagus at 54, according to the original intent and purpose of the apparatus. Then, upon inflation of the cuff, supplied air will enter the trachea and, if the nasal cavity 56 is sealed as by a nose clip 57, and if the oral cavity is sealed at the mouth, as by an appropriate mask, supplied air will enter the lung.

In order to avoid the difficulty, delay and inherent risk in the aforementioned procedure with the aforementioned apparatus, the apparatus of the FIGS. 1 and 2 embodiment of the present invention is adapted so that the longitudinal spacing of the distal ends of the two tubes will accommodate entry of the tip 13 into either the esophagus or larynx and, depending upon which passageway is entered, the lumen of one or the other of the tubes can be used to supply air to the lungs. The lumen of the other tube can be used for evacuation from or introduction of material to the stomach.

In the illustrated example, the tube 11 has properly entered the esophagus. The balloon 31 was inflated by pushing inward the plunger of the syringe 36, thus sealing tube 11 to the esophagus wall. Air is then supplied to the patient by a ventilating machine 38, or can be supplied by use of the self-expanding breathing bag 43, or orally by the attendant. If it is found that, contrary to the original intent, the tube 11 has entered the larynx, air can be supplied to tube 11 through the connector 16 by either the use of the machine or the bag or orally.

The particular location of the tube 11 after insertion can be observed by first leaving the proximal ends of both of the tubes 11 and 12 open, inflating the cuff 31, and blowing into the tube 12. If the chest expands, then proper insertion has been achieved, and the ventilating apparatus can be connected to the fitting 19. If the chest does not expand then the technician should blow into the tube 11. If the chest expands, then the breathing apparatus should be secured to that tube, and tube 12 is available for aspirating materials from the mouth and upper airway.

In view of the foregoing, safe ventilation can be reliably achieved promptly by one who is somewhat inexperienced with intubation procedures, if such person can recognize pulmonary ventilation through watching the chest expand, noting the presence of breath sounds, or condensation of vapor in the walls of one of the tubes, or noting the proper feel of air exchange. The provision of two tubes with standard connectors and a longitudinally adjustable collar 21 makes it possible to readily adjust to different sizes of patients and locate in the optimum position for each patient, as does the universal strap-retaining slot in the collar, permitting the strap to be pulled to a very small circle for a small patient. Also, the tubes can be made in smaller diameter and lengths for smaller patients. The provision of apertures in the walls of both tubes, proximate the end apertures, assures adequate openings to the lumens, even if the end aperture might be clogged or engaging a surface. The provision of the distal portions of the two tubes in substantially the same plane, such as the plane of the paper in the illustration of FIG. 1, tends to promote the desired reception of tube 11 in the esophagus; but the axial space between the upper edge 30 of sleeve 29, and the stop collar 21, and the flexibility of the tubes, permits them to be bent into a plane perpendicular to the paper at the collar. This enables them to be received between the teeth of the subject, without the mouth being propped open excessively, thereby facilitating the sealing of the lips with a comparatively small collar such as 21. The position of tube 12 inside the curve of tube 11 assists the sleeve 29 in keeping the tubes in close side-by-side relationship throughout a substantial portion of their length, from the distal end of the tube 12 to a point between the collar 21 and the proximal end 30 of the sleeve 29, where the tubes separate in order that each of them can be independently and individually adjustable with respect to the collar itself, and to each other without there being any leakage through the collar where the tubes pass through it.

Figure 3:
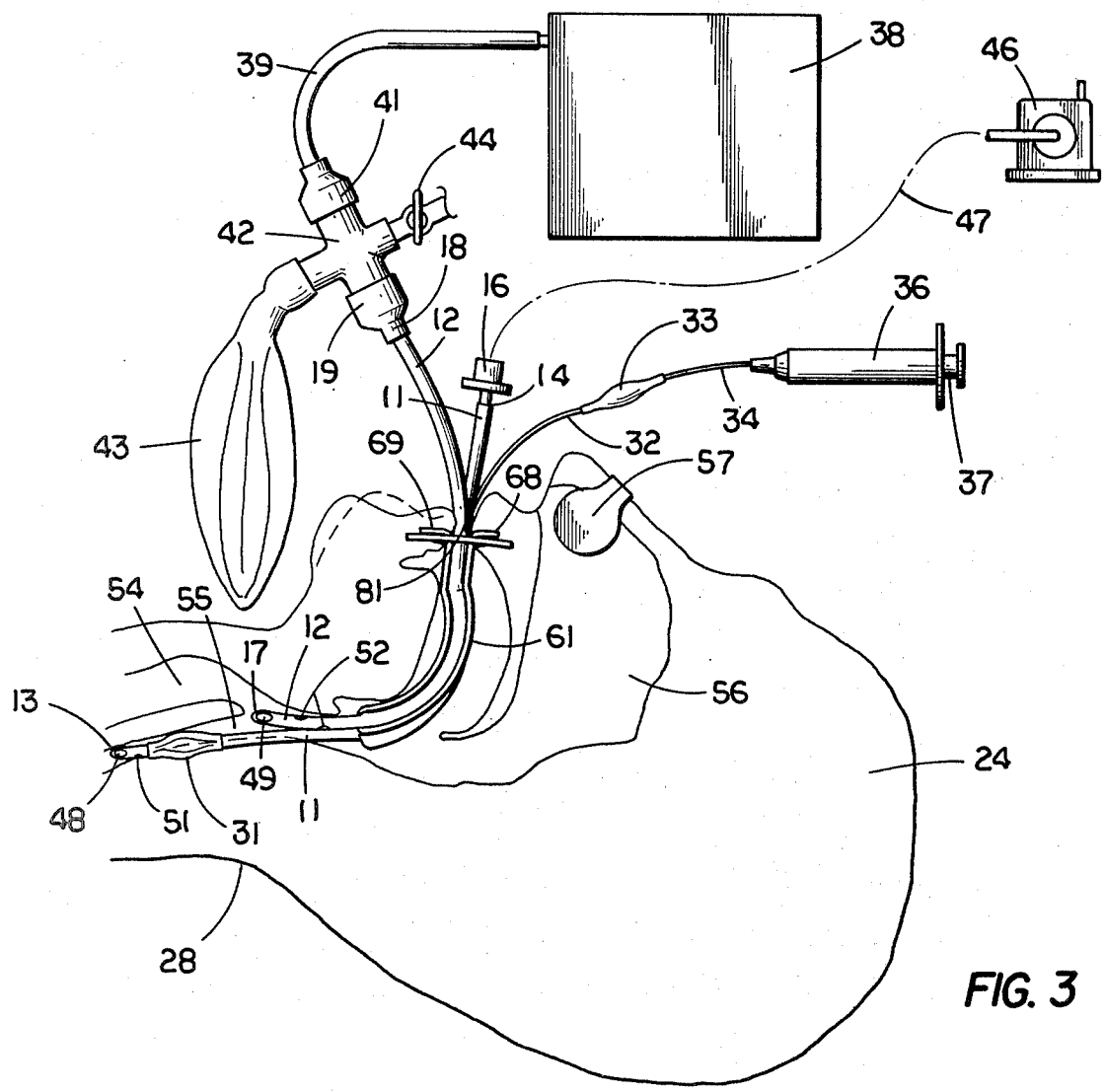
FIG. 3 is a view of the apparatus of the preferred embodiment of the invention, in use.

Referring now to FIG. 3, wherein most of the features and details may be the same as in FIG. 1 and are therefore given the same reference numerals, the sleeve 29 is omitted. Instead, there is a guide member 61, certain details of which can be better appreciated upon reference to FIGS. 4 through 8. Articles of somewhat similar configuration are available on the market and referred to as airways. One example of a somewhat similar device is the air tube 20 in U.S. Pat. No. 3,730,179 which discloses a combination resuscitating, aspirating and gastric draining apparatus. Instead of being a tube, the device on the market which is modified according to the present invention, has a pair of channels 62 and 63 (FIG. 8) with a common wall 64 extending from the proximal end 66 to a point near the distal end 67. Locator flanges 68 and 69 extend in opposite directions in a plane at the proximal end. According to one feature of this embodiment the present invention, the walls of each of the channels such walls 71 and 72 of channel 63 are curved toward each other as at 73 and 74 at their outer edges. In this way they securely retain the tubes therein. The resulting, generally c-shaped cross sectional configuration of each of the channels is provided from the proximal end flanges to the distal end. The tubes 11 and 12 are securely laterally retained in the channels. Although the tubes may be of PVC and the channel member of polyethylene, they are snug enough in the channels that, due to friction, they will not slide lengthwise in the channels, unless intentionally pushed or pulled.

Another variation from a standard airway is incorporated according to another feature of this invention. This is the diverging exit ends of the channels. Each of the channels has an axis which, while curved, lies in a plane. Therefore it is a curvilinear axis. For channel 62, the curvilinear axis is designated by a reference numeral 76. For channel 63, it is designated by reference numeral 77. These axes are in parallel planes and have the same shape except at the distal end of the member where, although the axes remain in the same parallel planes, they diverge as best shown in FIGS. 3, 4 and 6.

The purpose of this will be apparent as the description proceeds.

The common wall 64 of the two channels of the airway, which can be purchased, has a plurality of longitudinally spaced apertures 78 therein. The wall thickness of the common wall or web 64 may be 3 to 5 mm, as is true of the flanges 68 and 69 and the other channel walls such as 71 and 72. Therefore the guide member is semi-rigid, even if made of polyethylene, but the apertures avoid complete rigidity and provide some accommodation as the member is inserted into the oral cavity even in here the channel walls are curved according to my invention.

A lip seal 79 is snugly received on the outside of the guide member, immediately adjacent the flanges 68 and 69. This may be made of a soft plastic material to conform to the interior contours of the mouth, and also to conform to the outside shape of the guideway and the tubes received therein to provide a substantially airtight seal around them.

The method of use of the preferred embodiment of the apparatus is similar to the method described above for the embodiment of FIGS. 1 and 2. In this instance, however, the two tubes are normally located in the guide member with the distal ends of the two tubes substantially flush with the exit ends of the guideway near the distal end 67 of the guide member. The guide member is then placed in the oral cavity with the flanges 68 and 69 and lip seal 79 in place between the teeth and the lip as shown in FIG. 3. The distal end is in the pharynx substantially as shown. Then the tube 11 is pushed downwardly in the guide member and is directed posteriorly by the particular direction of the axis 76 of exit end of the guideway 62 so that it enters the esophagus as shown. Although this particular tube is the one with the cuff on it, it will slide in the guideway, and from the guideway it will slide readily into the esophagus since it is directed posteriorly, and the likelihood of it entering the trachea is minimal. If any difficulty is encountered in sliding it, this can usually be solved by simply wiggling the guide member slightly. When a sufficient length of tube 11 has been pushed in to be sure it is in the esophagus, the cuff is inflated. Then air can be introduced into tube 12. This tube can also be pushed downwardly in the guideway if needed, and as needed, in order to provide free flow of air. It may not be necessary to push the tube in at all in some subjects.

As in the previously described embodiment, if it happens that the lungs do not inflate upon supplying air through tube 12, then air is promptly supplied through tube 11 which has inadvertently entered the trachea. As mentioned above, this is highly unlikely with this embodiment of the invention, in view of the posterior direction of the exit of the guideway for the esophageal tube. In contrast, the exit end of the guideway for the endotracheal tube is directed anteriorly to orient that tube toward the trachea as shown in FIG. 3.

The size of guide member and amount of length of the tubes admitted to the subject will depend upon the size of the subject being treated. The length of the guide member from the flange 68 to the distal end is 12 cm. or less, while the length of admission of tube from the flange to the distal end of the esophageal tube, for example, would be about 30 cm. maximum in an adult person. As mentioned above, the lip seal member 79 is comparatively soft and formed to fit snugly around the guide member and tubes 11 and 12 in the guideways to minimize any air leak between the seal member and the tubes, and permit a buccal flap seal. Since it typically is not necessary to advance the distal end of the endotracheal tube 12 much, if any, beyond the distal end of the guide member, its overall length can be shorter than that of the esophageal tube and may be 15 cm. in overall length, compared to the usual 30 cm. or more overall length of the esophageal tube. Of course, the tube lengths are not critical, so long as there is at least some indication on tube 11, such as a marker line 81, to indicate how much tube has advanced beyond the lips of the subject. For smaller subjects, the guide member 61 may be shorter in overall length, and possibly smaller in cross sectional size.

It is believed that the foregoing description will reveal the advantages of the present invention as an apparatus for emergency ventilation of unconscious people, requiring less skill for inserting, no instruments to open and expose the airways, reducing the risk of the subject aspirating gastic contents, providing a diverting channel for vomitous, and providing a lumen to insert a suction catheter into the throat to clear secretions. Although there is a risk of laryngospasm in the event the patient is too responsive to inadvertent insertion of the tube 11 into the larynx, and although ventilation of the stomach can occur if the air supply is connected to the wrong tube, these risks are virtually negligible by comparison with the advantages achievable by the adoption and use of the present apparatus according to the procedure of the present invention.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

The invention claimed is:

1. Resuscitation apparatus comprising:
   first and second curved resilient tubes, each tube having a proximal end and a distal end, said tubes being in side-by-side relationship throughout a portion of their length, with the distal end of the second tube spaced lengthwise of said first tube from the distal end of said first tube,
   an external inflatable cuff on said first tube between the distal end of said first tube and the distal end of said second tube,
   cuff inflating means extending from said cuff to a point near the proximal end of said first tube, and
   a guide member having first and second curvilinear guideways therein receiving said tubes therein, said first tube being longitudinally and guidedly slidable in said first guideway for direction to the esophagus of a subject to be treated,
   said guide member having a proximal end and a distal end and a locator flange remote from the distal end, said guideways having the same curvatures throughout most of their lengths from the proximal end toward the distal end of said member, and each of said guideways having a curvilinear longitudinal axis in a plane parallel to a longitudinal axis plane of the other guideway, each of said guideways having an exit end at the distal end of said guide member, with said exit ends remaining in said plane but having diverging axes.

2. The apparatus of claim 1 wherein:

said guideways are oppositely facing grooves having a common wall.

3. The apparatus of claim 2 wherein:

both of said tubes are slidably received in said guideways but normally frictionally retained in their respective guideways, and slideable lengthwise therein from positions wherein the distal ends of said tubes are flush with the distal end of said guide member, to positions where the distal ends project lengthwise outward from the distal end of said guide member and are advanced to the said positions of lengthwise spacing of distal ends of said tubes.

4. The apparatus of claim 2 wherein:

said guide member is semi-rigid and pre-formed.

5. The apparatus of claim 1 wherein:

there is a lip seal sealingly mounted to said member and sealed to said flange.

6. A resuscitation apparatus guide member comprising:

a pair of oppositely facing curvilinear guide channels having a common wall from one end to a point adjacent the other end, said guide channels having axes lying in parallel planes and diverging at said other end, from said point.

7. The member of claim 6 wherein:

said guideways have cross sectional shapes at spaced points along the length of said guideways, said shapes including channel walls having outer edges directed toward each other.

8. The member of claim 6 wherein:

a locator flange is at said one end.

* * * * *